United States Patent [19]

Hlavacek et al.

[11] Patent Number: 4,792,336

[45] Date of Patent: Dec. 20, 1988

[54] FLAT BRAIDED LIGAMENT OR TENDON IMPLANT DEVICE HAVING TEXTURIZED YARNS

[75] Inventors: Robert A. Hlavacek, New Haven; Barry L. Dumican; Edward J. McCusker, both of Fairfield, all of Conn.

[73] Assignee: American Cyanamid Company, Stamford, Conn.

[21] Appl. No.: 835,493

[22] Filed: Mar. 3, 1986

[51] Int. Cl.⁴ .............................................. A61F 2/08
[52] U.S. Cl. .......................................... 623/13; 623/1; 623/66; 128/335.5; 128/334 R; 87/7
[58] Field of Search ................ 128/334 R, 335, 335.5, 128/92 YR, 92 YQ, 346, 334 C; 623/13, 66, 1; 87/7, 8

[56] References Cited

U.S. PATENT DOCUMENTS

| | | | |
|---|---|---|---|
| 2,940,247 | 6/1960 | Kirschbaum | 128/335.5 |
| 3,176,316 | 4/1965 | Bodell | 128/334 R |
| 3,463,158 | 8/1969 | Schmitt et al. | 128/334 R |
| 3,745,590 | 7/1973 | Stubstad | 623/13 |
| 3,982,543 | 9/1976 | Schmitt et al. | 128/335.5 |
| 4,300,565 | 11/1981 | Rosensaft et al. | 128/335.5 |
| 4,340,091 | 7/1982 | Skelton et al. | 623/1 X |
| 4,345,339 | 8/1982 | Muller et al. | 623/13 |
| 4,642,119 | 2/1987 | Shah | 623/13 |
| 4,652,264 | 3/1987 | Dumican | 623/1 |

FOREIGN PATENT DOCUMENTS

| | | | |
|---|---|---|---|
| 0122744 | 10/1984 | European Pat. Off. | |
| 0073454 | 10/1916 | Switzerland | 87/7 |
| 2151487 | 7/1985 | United Kingdom | |
| 2159846 | 12/1985 | United Kingdom | |

OTHER PUBLICATIONS

Cabaud et al., "Acute Anterior Cruciate Ligament Injury and Repair Reinforced with a Biodegradable Intra-articular Ligament", American J. of Sports Medicine, vol. 10, No. 5, (1982), pp. 259–264.

Primary Examiner—Richard J. Apley
Assistant Examiner—Paul Prebilic
Attorney, Agent, or Firm—Charles F. Costello, Jr.

[57] ABSTRACT

A surgical repair device having a length to width ratio of greater than one is disclosed. The device comprises a plurality of fibers. The majority of the fibers are in a direction essentially parallel to the device length.

The device has an absorbable component comprising a glycolic or lactic acid ester linkage. The remainder of the device, if any, has a non-absorbable component. The device can be used as a flat braid in the repair of a ligament or tendon.

1 Claim, 2 Drawing Sheets

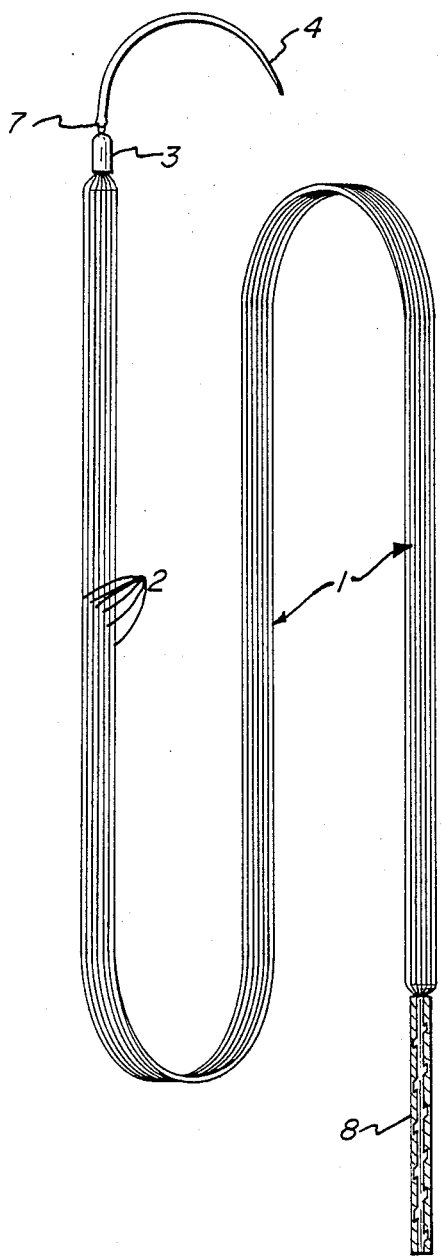
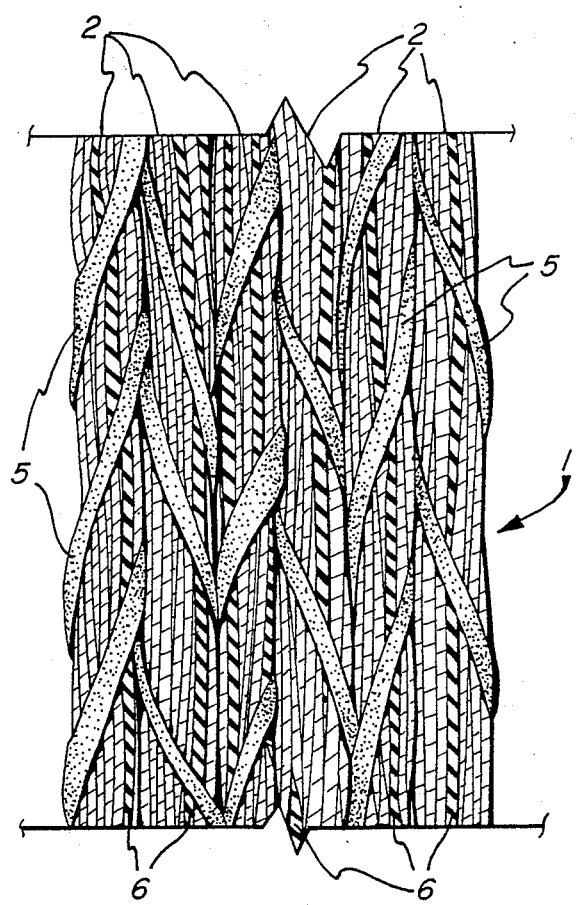
FIG. 1
FIG. 2

FLAT BRAIDED LIGAMENT OR TENDON IMPLANT DEVICE HAVING TEXTURIZED YARNS

BACKGROUND OF THE INVENTION

This invention relates to an implantable device composed of one or more bio-absorbable polymer(s) or combinations of bioabsorbable/non-absorbable polymer(s) for the repair or augmentation of connective tissue damaged by disease or injury. The devices shall serve as scaffolds for ingrowth and orientation of new fibrous connective tissue, (e.g. ligaments, tendons) in both intra-articular and extra-articular sites by maintaining structural stability during initial healing and then undergoing at least partial gradual absorption to prevent stress shielding and allow newly formed tissue to become correctly oriented and load bearing.

The invention includes several aspects of device design that are intended to provided for simulation of natural tissue function immediately after implantation and to support subsequent fibrous tissue ingrowth as well as orientation in the direction of natural loading. The devices are braided or woven into a flat tape geometry having the plurality of fibers aligned in parallel to form the axial warp. The physical/mechanical/chemical properties of all or part of the component fibers may be enhanced by a number of temperature/time/stress treatments. One or more adjacent plies of the device are used in surgery to achieve biomechanical properties approximately equivalent to the healthy tissue prior to being damaged. A swivel needle attachment system may be incorporated to facilitate handling and surgical placement of the devices. The interfibrillar space, that provides for initial tissue ingrowth, occurs as a result of the braiding/weaving process or may be enhanced by means of texturizing the yarns. Gradual bioabsorption, in whole or in part, provides for additional interfibrillar space to form during the healing period, and for fibrous tissue orientation to be induced as load is transferred from the weakened implant to the 'neo-ligament' or 'neo-tendon'.

The bioabsorbable materials, biocompatible nonabsorbable materials, physical and chemical combinations thereof, and the processes involved in fabricating them into the implantable devices are all included in this invention.

Ligaments and tendons are bands or sheets of fibrous connective tissue which provide support and stability to the musculoskeletal system. Relief of the pain and/or instability caused by damage to a ligament or tendon is currently achieved by techniques ranging from simple suturing to removal and replacement with other tissue or a permanent synthetic prosthesis. Although no single technique is appropriate for all situations, it is generally preferred to return the tissue to it's healthy, pre-damaged state as naturally as possible. Furthermore, it is highly desirable to reduce the need for activity restriction during the healing period. The permanent retention of implanted foreign materials is considered undesirable and should be minimized because it may result in stress shielding and subsequent atrophy of natural tissue, or the migration of the materials to other tissues and/or systems (i.e. lymphatic) may occur.

The state-of-the-art in ligament repair/reconstruction is considered to be the use of autogenous tissue grafts for augmentation or replacement of the damaged ligament. Portions of the patellar tendon, iliotibial band, semitendinosus tendon, and fascia lata are some of the most commonly used autogenous tissue grafts. Due to the undesirability of having to sacrifice one tissue and its associated function, in order to repair another, a number of synthetic, permanent total ligament prostheses and ligament augmentation implants are being tried in animals as well as clinically.

Several of the permanent ligament prostheses are fabricated so that the properties of a single synthetic material characterize the implant's response to in-vivo loading (see e.g., U.S. Pat. Nos. 3,896,500; 3,953,896; 3,987,497; 3,988,783; and European Patent Applications Nos. 51,954; 106,501; and 126,520, all of which are incorporated herein by reference). Although many of the aforementioned patents include more than one material in the structure of the body of the prosthesis, a single material determines the mechanical (tensile) properties while the secondary components are in the form of coatings, sheaths, etc. to improve biocompatibility or lubricity. While ligamentous tissue is a natural composite material exhibiting both compliant elasticity and high longitudinal strength, no single synthetic biocompatible material has this combination of properties. As a result, implants such as the ones listed above have tended to fail in animal or clinical trails either by material fatigue, creep (joint laxity), in-vivo degradation or by unacceptable restriction of joint motion.

A number of multi-component ligament prostheses (see, e.g. U.S. Pat. Nos. 3,797,047; 4,187,558; 4,483,023; and European Patent Application No. 122,744, all of which are incorporated herein by reference are more bio-mechanically compatible with the elasticity and strength requirements of natural ligament function but suffer from other shortcomings. Since they are designed to replace the natural ligament, any reparative tissue that forms at the site of the defect, is almost completely shielded from applied loads and therefore tends to resorb. The inevitable chemical and/or physical breakdown of these implants in-vivo, leads to catastrophic failure and a return to pre-operative instability, or worse, because no natural tissue repair has taken place. No ligament prosthesis, tried thus far in animals or humans, has yielded consistently acceptable joint stability without the occurrence of implant breakdown, synovitis, and/or articular tissue damage during the first two years post operatively. The desired minimum post operative period of implant/joint stability is 10 years.

Attempts at a long-term 'natural' tissue repair (by augmenting but not replacing the natural tissue) has been approached by the use of a variety of devices and techniques. The use of a permanent device for augmentation of an autogenous tissue transplant is described in "Experimental Mechanical and Histologic Evaluation of the Kennedy Ligament Augmentation Device", G. K. McPherson, Ph.D. et al., Clinical Orthopedics and Related Research, no. 196, pages 186 to 195, 1985, which is incorporated herein by reference. While the method of attachment allows the desired natural tissue repair to occur, the entire synthetic implant remains in situ; some interfibrillar mechanical breakdown has recently been reported, and a chronic foreign body response is observed even at 2 years following implantation. A biologically mechanically degradable augmentation device consisting of polyglycolic acid (herein abbreviated as PGA)—coated carbon fibers (U.S. Pat. No. 4,411,027) or polylactic acid (herein abbreviated as PLA)—coated carbon fibers (U.S. Pat. No. 4,329,743)

has also met with limited success in obtaining a 'natural' tissue ligament repair. Both of these patents are incorporated by reference. However, even though the polymer coating protects the brittle carbon fibers intra-operatively and is then safely absorbed by the body, the gross modulus and elasticity mis-match between the carbon fibers and the new ligamentous tissue that infiltrates the implant, results in fragmentation of the carbon fibers. This mechanical breakdown of the carbon fibers does serve to transfer load to the new tissue as desired, but serious concerns persist regarding the eventual disposition of the carbon fiber fragments. Finally, as described in "Acute Anterior Cruciate Ligament Injury and Repair Reinforced with a Biodegradable Intraarticular Ligament", H. E. Cabuad, M. D. et al., The American Journal of Sports Medicine, vol. 10, pages 259 to 265, 1982; and "A Partially Biodegradable Material Device for Repair and Reconstruction of Injured Tendons: Experimental Studies", W. G. Rodkey, D.V.M. et al., AAOS Meeting, 1985, both of which are incorporated herein by reference, and the comparative examples A to F herein, biodegradable implants consisting of PGA and polyester (specifically Dacron TM) have been tried as repair/augmentation devices for obtaining 'natural' ligament and tendon healing. The results of this work indicate that PGA does not retain its properties long enough, in-vivo, and that any tissue that does infiltrate the permanent polyester fiber component does not achieve adequate strength or joint stability due to lack of tissue orientation and excessive ligament/tendon lengthening. The relatively short strength retention period of PGA, will apparently not allow the elimination of joint immobilization that is currently necessary following ligament repair or reconstruction.

The surgical repair device of this invention has functional advantages over the implant device described in European patent (hereafter EP) Application No. 122,744. For example, this invention can utilize absorbable fibers in the axial (lengthwise) direction. The majority of absorbable fibers in the axial direction enhances or essentially guarantees the transfer of the connective tissue stress from the device to the ingrowing collagen fibers. In summary, with the majority of fibers being in the axial direction and with these fibers being at least about 80% absorbable fibers, there appears to be more tissue ingrowth and better oriented collagen fibers.

This invention is useful as a temporary or augmentation device. In this utility, it seems to match as closely as possible the biological properties of a connective tissue until ingrown collagen fibers can replace the majority of fibers (preferably having an absorbable component comprising at least about 80 percent) in the axial direction. The advantage of this invention, e.g. over the implant device disclosed in EP Application No. 122,744, is that it appears to provide a surgical repair device (specifically for connective tissue, and more specifically for ligament or tendon repair) that will have the correct stress related properties to act as a connective tissue (until living tissue can replace the device). This is accomplished by the ingrown collagen fibers replacing the absorbable fibers in the axial direction. The use of nonabsorbable fibers is as a support or backbone for the absorbable fibers.

This invention has superior and unexpected structural properties over those disclosed in the prior art, specifically EP Application No. 122,744. For example, the majority of the fibers in this invention, that is 50 percent or more, are in the axial (lengthwise) direction. Preferably, 80 to 95 percent are in the axial direction. This approximately twofold increase of fibers in the axial (lengthwise) direction (over the axial direction fibers in EP Application No. 122,744) is at least one of if not the primary reason for obtaining the functional advantages discussed above.

The surgical repair device of this invention has other advantages over the prior art. For example, the thickness of the device is smaller than the known prior art devices. This is because the majority of the fibers are in the axial direction. The smaller thickness allows this device to be useful in more constricted connective tissue repair procedures. Also, as a general statement, the smaller the thickness or width of the repair device, the greater is its utility as a temporary or augmentation device because tissue ingrowth is facilitated. Conversely, the larger the thickness or width of the device, the more it is used as replacement (that is, as a permanent implant) rather than a temporary device.

It is, therefore, the object of this invention to provide sterile, surgically implantable devices, means for surgical placement/attachment, and fabrication processes that are uniquely suited for providing the most advantageous connective tissue (i.e. ligament, tendon, etc.) repair. These implants resolve the apparent disadvantages of the devices described above by: 1. providing adequate strength and stiffness immediately post-operatively to minimize or eliminate the need for immobilization; 2. facilitating the ingrowth of vascularized cellular tissue by reason of the open flat tape configuration; 3. supporting the proper orientation of collagen fibers formed within and around the implant through the predominantly axial alignment of the component yarns and the gradual transfer of applied loads from the biodegradable yarns to the newly formed tissue; 4. providing a longer lasting bioabsorbable material to permit adequate time for new tissue ingrowth or revascularization of autogenous tissue grafts or allografts; 5. providing a complaint, elastic, permanent component to protect tissues from over-load, without stress-shielding, for a longer term than provided by the bioabsorbable materials, in those applications (i.e. some intraarticular ligament reconstructions) where healing occurs more slowly; and 6. avoiding the use of materials which fragment and pose risks of migration to adjacent tissues.

The object of this invention comprises bioabsorbable or combined bioabsorbable/biocompatible polymers fabricated into an elongated textile structure having means for surgical placement/attachment at one or both ends for the purpose of repair, augmentation or replacement of damaged connective tissues, such as ligaments and tendons.

SUMMARY OF THE INVENTION

A surgical repair device having a length to width ratio of greater than one has been invented. The device comprises a plurality of fibers. The majority of the fibers are in a direction essentially parallel to the device length.

The device has an absorbable component comprising from about 10 to 100 percent of polymer having a glycolic or lactic acid ester linkage. The remainder of the device, if any, has a nonabsorbable component.

In one embodiment of the device, the absorbable polymer is a copolymer having a glycolic acid ester linkage. In a specific embodiment, the copolymer comprises glycolic acid ester and trimethylene carbonate linkages.

A connective tissue repair device having a length to width ratio of greater than one has also been invented. The device comprises a plurality of fibers. The majority of the fibers are in a direction essentially parallel to the device length. The device has an absorbable component comprising from about 10 to 100 percent of a copolymer. The copolymer has glycolic acid ester and up to about 50 percent by weight of trimethylene carbonate linkages. The remainder of the device, if any, has a nonabsorbable component.

Embodiments of the repair device include a knitted, woven, braided and flat braided device. In one embodiment, the longitudinally oriented majority of the fibers comprises about 80 to 95 percent. In a specific embodiment, the longitudinally oriented majority of the fibers comprises about 90 percent.

In another embodiment, the device has an absorbable component comprising at least about 80 percent. In a specific embodiment, the device has a nonabsorbable component selected from the group consisting of a poly($C_2$–$C_{10}$ alkylene terephthalate), poly($C_2$–$C_{10}$ alkylene), polyamide, polyurethane and polyether-ester block copolymer. In a more specific embodiment, the device consists of poly(ethylene terephthalate) or poly(butylene terephthalate) as the poly($C_2$–$C_{10}$ alkylene terephthalate), and a polybutester as the polyether-ester block copolymer. In a most specific embodiment, the device consists of Hytrel ® as the polybutester.

A polybutester can be defined as a polytetramethylene glycol, polymer with terephthalic acid and 1, 4-butanediol. See, e.g., the definition of polybutester in USAN and the USP dictionary of drug names, U.S. Pharmacopeial Convention, Inc., Md. 20852 U.S.A., 1985.

Hytrel ® is a trademark of E. I. du Pont de Nemours & Co., Wilmington, Del. U.S.A. for a class of polymers having the following generic formula:

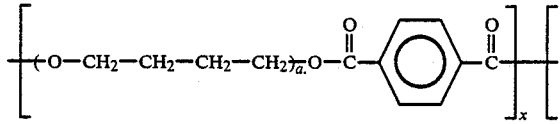 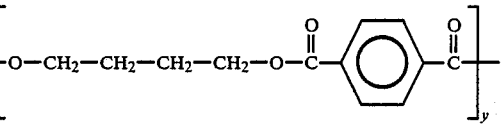

polytetramethylene glycol terephthalate  polybutylene terephthalate

The values for a, x and y are known from the prior art, e.g. as disclosed in "Thermoplastic Copolyester Elastomers: New Polymers For Specific End-Use Applications", M. Brown, Rubber Industry 9 102–106 (1978), and the references (footnote numbers 1b, 1c, 1d, 2 and 3) cited therein; Encyclopedia of Polymer Science and Technology, Supplement, 2 485–510, see particularly pages 486 to 493, Interscience N.Y. 1977; and U.S. Pat. No. 4,314,561 issued Feb. 9, 1982. All of this prior art is incorporated herein by reference. A specific embodiment of Hytrel ® which is useful in this invention is a grade of Hytrel ® having a 72 durometer D. hardness. The polymer in the NOVAFIL ® (American Cyanamid Company, N.J., U.S.A.) surgical suture contains Hytrel ®.

A flat braided ligament or tendon implant device having a length to width ratio of greater than one has been invented. The device comprises a plurality of fibers. The majority of the fibers are in a direction essentially parallel to the implant length. The braid has about 5 to 100 carrier and up to about 50 warp yarns.

The implant has an absorbable component comprising from about 10 to 100 percent of a copolymer. The copolymer has glycolic acid ester and from about 20 to 40 percent by weight of trimethylene carbonate linkages. The remainder of the implant, if any, has a nonabsorbable component.

In one embodiment of the implant, the braid has about 13 carrier and about 6 warp yarns. In a specific embodiment, the implant consists of about 100 percent of the absorbable component. In a more specific embodiment, the carrier yarns consist of about 100 percent of the absorbable component and the warp yarns comprise about 80 percent of the absorbable component. In a most specific embodiment, the nonabsorbable component in the warp yarns is selected from the group consisting of a poly(ethylene terephthalate) and polyether-ester block copolymer.

In other embodiments of the implant, the yarns are texturized or heat treated. In a further embodiment of the implant, the braid is heat treated.

The bioabsorbable filaments may be comprised of man-made polymers including glycolide-trimethylene carbonate (GTMC), polyglycolic acid, polydioxanone, poly(L-Lactic) acid, poly(DL-Lactic) acid and copolymers or physical combinations of the components of these polymers. Natural bioabsorbable polymers such as regenerated collagen or surgical gut may also be used. The biocompatible (nonabsorbable) components include poly(ethylene terephthalate) (PET), poly(butylene terephthalate) (PBT), polyether-ester multi-block copolymers, polypropylene, high strength/modulus polyethylene, polyamide (including polyaramid), or polyether type polyurethanes. Once spun into filaments, the properties of the above materials may be improved for this application by various temperature/time/stress treatments.

The device shall be braided, woven or knitted so that the structure has the desired strength and stiffness in the primary (axial) loading direction. It also has adequate interfibrillar space and minimized thickness to promote the ingrowth of tissue. The end(s) of the device may be compressed inside biocompatible metal sleeve(s) to which swivel end-caps(s) and surgical needle(s) are attached in such a way as to permit rotation of the needle(s) about the longitudinal axis of the device.

In use, an appropriate number of plies of the device are implanted to match the biomechanical properties of the tissue being repaired. This permits an early return to normal function post-operatively. As the ligament or tendon begins to heal, the implant continues to bear any applied loads and tissue ingrowth commences. The mechanical properties of the bioabsorbable component(s) of the implant then slowly decay to permit a gradual transfer of loads to the ingrown fibrous tissue, stimulating it to orient along the loading direction. Additional ingrowth continues into the space provided by the absorbed components of the implant. This process continues until the bioabsorbable component(s) are completely absorbed and only the newly formed tissue remains, or the biocompatible (nonabsorbable) component(s) are left in situ to provide long-term augmentation of the newly formed tissue.

BRIEF DESCRIPTION OF THE DRAWINGS

FIG. 1 is a diagrammatic view of the device described as the preferred embodiment, except that two different possible ends are shown.

FIG. 2 is an enlarged view of the flat surface of the preferred embodiment showing the braided construction in greater detail.

DESCRIPTION OF THE PREFERRED EMBODIMENT

In preferred embodiments the elongated textile structure 1 of the implant comprises a flat braid having primarily axial (quoit) yarns 2 of an absorbable polymer such as GTMC. The number and denier of quoit and sleeve yarns are varied to provide devices having a range of properties that are biomechanically compatible with any likely implant site. Swivel end cap(s) 3 and surgical needle(s) 4 may be attached at the end(s) of the device to facilitate placement and attachment.

Figure 3:
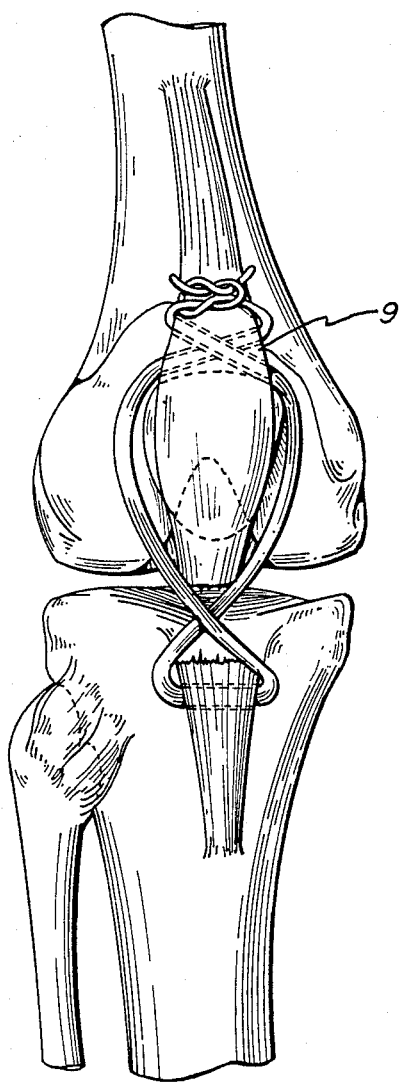
FIG. 3 is an anterior view of a knee showing the device as positioned for repair of the excised patellar ligament in animal (canine) studies.

The procedures described below are followed when preparing flat braids to be used as artificial ligaments/tendons starting from the appropriate yarns. To begin, the proper denier yarns for the specific braid construction are required. This example describes a typical construction designed to fit a particular animal model—repair/replacement of the canine patellar ligament (FIG. 3). An application that had a tensile strength/stiffness requirement three times higher than that described in the example would require three times as much yarn. This could be accomplished by simply tripling the final total braid denier, either by increasing the yarn denier or increasing the number of sleeve and quoit (stuffer yarns) or both.

To produce a braid for canine patellar ligament repair (FIG. 3), a final braid denier between 13,000 and 24,000 is targeted. In the preferred construction, approximately 90% of the fiber is contained in the parallel quoit or warp yarns 2.

The sleeve yarns 5, which consist completely of absorbable material, are generally about 130 denier. On transfer they are given a nominal 1.4 turn per inch (TPI) 'Z' or 'S' twist before further processing. This facilitates handling and minimizes fiber breakage. It is to be understood that the term "carrier" yarns, as disclosed for example in the above "SUMMARY OF THE INVENTION", is synonymous with the term "sleeve" yarns.

The quoit (stuffer or warp) yarns can be 100% absorbable or they may contain a nonabsorbable component. They are much heavier than the sleeve, generally ranging from 2100 to 2700 denier. This necessitates two passes on a six position ply twister. A 130 denier yarn would normally be 5-plied 2.8 TPI 'S' or 'Z', then 4 ends of the 5-ply yarn would be twisted 1.4 TPI in the reverse direction. This would result in a final quoit yarn denier of 2600, mechanically balanced from the reverse twist operation (no tendency to twist or unravel).

Nonabsorbable components 6, if included, are blended into the quoit yarns during the 1st ply twisting operation. For instance, a MAXON TM /NOVAFIL ® (American Cyanamid Co., N.J. 07470 U.S.A.) bicomponent yarn consisting of 18-22% nonabsorbable fiber would be made by running 1 yarn of 130 denier NOVAFIL ® with 4 yarns of 130 denier MAXON TM in the 5-ply operation. The preparation and polymeric composition of MAXON ® is disclosed in U.S. Pat. Nos. 4,429,080; 4,300,565 and 4,243,775; the preparation and polymeric composition of NOVAFIL ® is disclosed in U.S. Pat. Nos. 4,314,561; 4,246,904; and 4,224,946. All of these patents are incorporated herein by reference. The exact proportion of NOVAFIL ® is determined by the yarn deniers involved and the proportion of quoit yarns in the braid construction.

An important processing step for some absorbable yarns is post treatment (a vacuum annealing step which upgrades the implant tensile values). Generally speaking, for a construction that is to be 100% absorbable, the yarns are post treated after ply twisting; for an absorbable/nonabsorbable biocomponent construction, the absorbable yarns are post treated prior to ply twisting. There is another option and that is to post treat the final braid, providing it does not have a deleterious effect on a nonabsorbable component.

After ply twisting and post treatment, the yarns are ready for braiding. The best results to date are obtained with a construction that is made on a 13 carrier flat braider, which has 6 quoit yarn feeds. About 90% of the construction is composed of the heavy parallel quoit yarns held loosely together by the sleeve yarns at 12.3 picks (yarn cross-over points) to the inch.

After braiding, the ligament is ready for further processing. It is cut to length and sleeved on both ends with a ¼" aluminum or silver sleeve. A stainless steel over cap 3 with a small metal swivel pin 7 is then attached.

The end capped ligaments are now ultrasonically washed in xylol to remove any residual finishing oils (6 min residence in each of 4 baths). After the implants are air dried, appropriate needles 4 are attached to the metal pins to allow the implant to swivel in use.

They are then packaged in preformed plastic trays with a lid and in open aluminum foil laminate envelopes. They are sterilized in an Ethylene Oxide cycle which includes an elevated temperature vacuum drying step. The foil laminate envelopes containing the dry ligaments are then heat-sealed in an asceptic glove box hood fed by dry air. Any interim storage needed between vacuum drying and heat sealing is carried out in an asceptic sealed box fed, again, by dry air.

Figure 4:
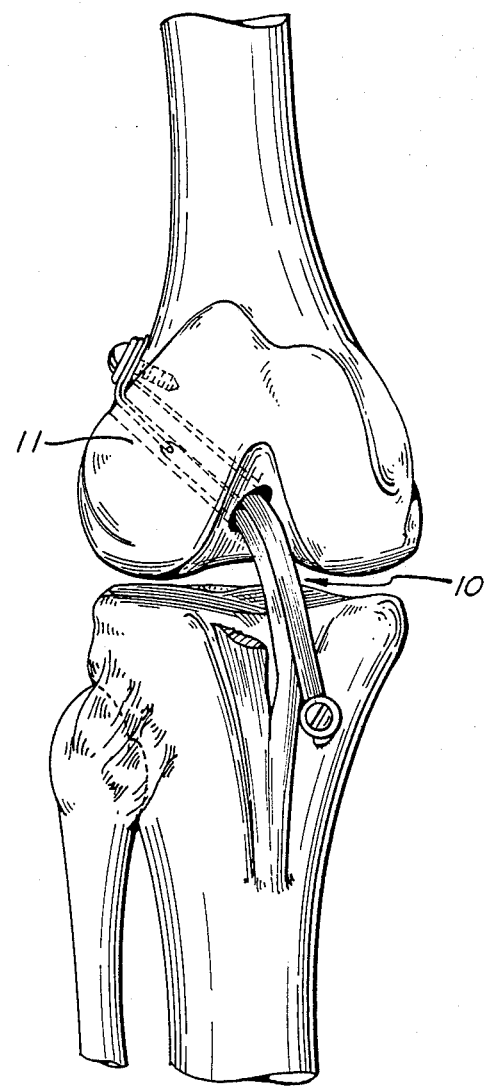
FIG. 4 is an anterior view of a knee showing the device as positioned for augmentation of the medial third of the patellar ligament in an Anterior Cruciate Ligament reconstruction.

Devices, as described above, may be surgically implanted to bridge a defect in a ligament, as a replacement for an excised damaged ligament (FIG. 3) or as an augmentation (FIG. 4) for autogenous tissue graft (or allograft) ligament reconstruction. In those surgical procedures requiring passage through and/or attachment to soft tissue 9, implants having the end-cap 3 and swivel needle(s) 4 at the end(s) would be used. For those applications in which the implant only needs to be passed through an open joint space 10 or through pre-drilled tunnels in bone 11, the swivel needles would not be required. Implants provided for such procedures may instead have either: (a) melt-fused ends to prevent fraying, or (b) ends stiffened by surrounding tubes 8 that are melt-fused or heat-shrunk onto the material of the device itself.

The invention can be described by the following examples.

EXAMPLE 1

The implant consists of 100% MAXON TM yarns in a 13 carrier flat braid construction. It was made from 100 denier/8 fil MAXON TM yarns that were post treated prior to twisting. Both sleeve and quoit yarns were twisted at 10 TPI to retain yarn integrity. The sleeve yarns consisted of 13 carriers holding 200 denier yarns made by 2-plying the 100 denier yarns. The 6 quoit or stuffer yarns were made by a double pass (6 yarns over 6 yarns) on the ply twister to form a 3600 denier yarn. The final braid denier was 24,200 with 89.3% of the fibers contained in the quoits. Picks/inch were calculated at 12.3.

The braid was then forwarded to an outside vendor to be cut to length and end capped. On return, the implants were washed ultrasonically in xylol, dried, needled and packaged. In this instance, packaging consisted of a 1 mil aluminum foil inner envelope, dry sealed after ETO sterilization and vacuum drying. Inner envelopes were then overwrapped in a TYVEK TM (E.I. du Pont de Nemours & Co., Del. 19898 U.S.A.) package prior to a 2nd ETO sterilization cycle.

Straight pull tensile strengths averaged at 203 lbs equivalent to 3.8 grams/denier with an extension to break of 33.4%. Hydrolytic strength data indicated that the device was viable and samples were implanted in 10 month or older beagle dogs replacing the canine patellar ligament. Sacrifices occurred at 2, 4 and 6 months. Histological examination indicated 50–90% infiltration of the device by cellular tissue and some collagen fiber at 2 months, and well organized collagen replacing the absorbed MAXON TM at 6 months. Some displacement of the patella was evident at 2 and 4 months, but 6 month x-ray data approximated the non-operated controls. 'Neo-ligament' cross sectional area at the 2 month interval was approximately 2 to 3 times that seen on the non-operated controls. The size of the tissue mass gradually decreased at subsequent post-operative evaluation periods. Final tensile strengths of excised ligaments ranged from approximately 180 lb. at 2 months, to approximately 250 lb. at 4 and 6 months, with extensions at break of 7.9 to 9.2 mm which are in the range of the unoperated controls.

EXAMPLE 2

This implant also consists of 100% MAXON TM in a flat braid construction. However, the source yarns were heat stretched at 32% prior to braiding and post treated after braiding. The construction itself consisted of 1-124d sleeve yarns twisted to 2.2 TPI 'S' and 6-2232d quoit yarns ply twisted as follows: first 3 yarns at 2.2 TPI 'Z' which were then reverse twisted—6 yarns at 1.1 TPI 'S'. The total final denier was 15,000 with 89.3% comprised of quoit yarns. This construction also had 12.3 Picks/inch.

This braid has a 148 lb breaking strength (equivalent to 3.94 grams/denier) with an extension at break of 26.2%. Hydrolytic data indicated the material was viable as an implant. Sterile devices of this type were prepared as in Example 1.

EXAMPLE 3

This implant was a MAXON TM /DACRON ® bicomponent in an approximately 80/20 blend. DACRON ® is a trademark of E. I. du pont de Nemours & Co., Delaware 19898 U.S.A, for a synthetic poly(ethylene terephthalate) fiber. Both components had been heat stretched at 18.5–20% prior to ply twisting. To make the quoit yarns, four yarns of 120d MAXON TM were twisted at 1.4 TPI 'Z' and then combined with 1 yarn of 127d DACRON ® (also twisted at 1.4 TPI 'Z') in a ply twisting operation at 2.8 TPI 'S'. Four of these bicomponent yarns were then reverse twisted at 1.4 TPI 'Z' for a total denier of 2428. The sleeve yarn was simply 120d MAXON TM twisted to 9.1 TPI 'Z'.

The flat braid was made on a 13 carrier machine with 6 quoit yarns at a 12.3 pick. Total denier was 16,128 with 90.3% of the total construction combined in the quoits. 18.9% of the total construction consisted of the nonabsorbable (DACRON ®) component.

This sample broke at 140 lbs (equivalent to 3.94 grams/denier) with a 24.2% breaking elongation. Hydrolytic data indicated the sample was viable. Samples were prepared as in Example 1, and implanted in 10 month or older beagle dogs replacing the canine patellar ligament. Histological evaluation of the repaired ligament at 2 months indicated the ingrowth of cellular tissue to be localized near the implant periphery. At subsequent post-operative intervals, collagen was observed as an oriented fibrous sheath surrounding the remaining Dacron ® yarns with minimal tissue infiltration or vascularization noted. However, the cross-sectional area, as well as the length of the neo-ligaments were substantially equivalent to those obtained with the device of Example 1. Average tensile strengths of the repaired ligaments at the 2, 4 and 6 month post-operative evaluation periods also ranged from approximately 180 lb. to 250 lb. The extensions at break for ligaments repaired with these particular devices were between 8 and 16 mm; generally greater than the unoperated controls.

EXAMPLE 4

This construction utilized heat stretched MAXON TM combined with NOVAFIL ® in an 80/20 combination. The sleeve yarn was simply 120d MAXON TM twisted at 9.1 TPI 'Z'. The quoit yarns consisted of 2 yarns of 68d NOVAFIL ® that had previously been ply twisted at 1.4 TPI 'Z' combined with 4 yarns of MAXON TM twisted to 1.1 TPI 'Z' prior to heat stretching at 20%. These yarns were ply twisted at 2.8 TPI 'S'. Four of these bicomponent yarns (of about 616 denier) were then reverse twisted at 1.4 TPI 'Z' to give a quoit yarn of 2464 denier.

These yarns were braided on a 13 carrier flat braider with 6 quoit ends at 12.3 picks/inch. Final braid denier was 16,344, of which 90.5% was contained in the quoits. Approximately 22.1% of the total construction was the nonabsorbable component-NOVAFIL ®.

The resulting ligament broke at 155 lbs (equivalent to 4.31 grams/denier). The extension at break was 27.4%. Hydrolytic tests indicated that this design was a viable one. After further processing, as in Example 1, devices of this type were implanted in 10 month or older beagle dogs replacing the patellar ligament. Compared to the repairs made with the devices described in Examples 1 and 3, these implants appeared to yield the best histological results. Approximately 70–90% of each of the implants had been infiltrated with well organized, vascularized, cellular tissue and some collagen fibers within 2 months. Results improved with time, so that at six months the non-absorbable NOVAFIL® yarns served as a scaffold that was completely infiltrated with well vascularized, axially oriented collagen fibers. The 'neo-ligament' cross-sectional area and length followed the same trends as in Examples 1 and 3. Tensile strengths gradually increased from approximately 180 lb. at 2 months to about 250 lb. at 6 months; well within the range of unoperated control strengths which averaged 220 lb. The extension-at-break remained fairly constant at 11-12 mm which, while generally greater than the unoperated controls was intermediate to the results noted in Examples 1 and 3.

Examples 5 to 10 were part of an experimental study designed to determine the effect of heat stretching and post treatment on MAXON ™. The net conclusion was that post treatment served to upgrade implant properties; heat stretching by itself or in combination with post treatment did not markedly improve MAXON ™ implant properties after sterilization.

EXAMPLE 5

This construction is also 100% MAXON ™ in a flat braid construction. The yarns were not heat stretched before braiding. The sleeve yarns consisted of 130d MAXON ™ twisted to 1.4 TPI 'S'. The quoit consisted of 5 yarns of 130d MAXON ™ twisted to 2.8 TPI 'Z'. Four yarns of this 5 ply construction were then twisted to 1.4 TPI 'S' for a total denier of 2600.

The above yarns were then braided on a 13 carrier braider with 6 quoit ends set at a 12.3 pick. The final construction came to 17,694 denier, of which 90.2% were quoit ends.

After sterilization this construction measured 19,134 denier. It had a 138 lb breaking strength (equivalent to 3.27 grams/denier) and an extension at break of 54.2%.

EXAMPLE 6

The same as Example 5 except that the yarns used were post treated before braiding.

The final denier was 17,550 which changed to 18,288 after sterilization. The sterile devices had a breaking strength of 126 lbs (3.13 grams/denier) with an extension at break of 38.1%.

EXAMPLE 7

The same as Example 5 except that the braid itself was post treated.

The final denier was 17,811 which changed to 18,414 after sterilization. Strength to break was 145 lbs (3.57 grams/denier) with an extension at break of 39.3%.

EXAMPLE 8

The same as Example 5 except that the ply twisted yarn was heat stretched at 26% before braiding. Material was not post treated either as a yarn or braid.

The final denier was 16,497 which changed to 19,332 after sterilization. Strength to break was 121 lbs (2.84 grams/denier) with an extension at break of 44%.

EXAMPLE 9

Same as Example 8 except that this yarn was post treated after heat stretching.

The final denier was 15,786 after braiding. On sterilization this changed to 18,034. The strength to break of the sterile devices was 135 lbs (3.41 grams/denier) with an extension at break of 34.2%.

EXAMPLE 10

Same as Example 8 except that the braid itself was post treated.

The final denier was 16,362 after post treating; 17,392 after sterilization. The strength to break of the sterile implants was 150 lbs (3.90 grams/denier) with an extension at break of 34.6%.

EXAMPLE 11

This embodiment consisted of 100% MAXON ™ in a flat braid construction. It differs from constructions described in previous examples in that it was airjet texturized prior to the initial twisting steps. The sleeve yarn consisted of 149d texturized MAXON ™. This was made by overfeeding 2 yarns of 66 denier MAXON ™ into the airjet chamber-one by 15% and the other by 8%. This material was then twisted to 1.4 TPI 'Z'. The quoit yarn started with 219 denier texturized MAXON ™. This was made by overfeeding 1 end of 66d MAXON ™ at 15% into the airjet along with 1 end of 130d MAXON ™ at 8%. The 219 denier yarns were then 3-plied at 2.8 TPI 'S'. Four yarns of the 3-ply material were then reverse twisted at 1.4 TPI 'Z' to give a final denier of 2523.

This material was braided on a 13 carrier flat machine at 12.3 picks per inch. Its final denier measured 17,693 with 88.7% of the construction in the quoits.

The straight pull to break averaged 130 lbs (3.3 gms per denier) with an extension at break of 26.7%. As expected, its surface appearance resembled that made of yarns spun from a natural, staple fiber such as cotton or wool. Optically, the braid could be characterized as having a loose, single fil looped appearance. Subsequent processing of the braid is as described above under the heading 'Description of the Preferred Embodiment'.

EXAMPLE 12

This design is identical to Example 11 except that in the initial 3-plying of the quoit yarns one end of a 245 denier MAXON ™/NOVAFIL® texturized bicomponent yarn was substituted for one of 219 denier texturized MAXON ™ yarns. This MAXON ™/NOVAFIL® bicomponent was made by overfeeding a 66d MAXON ™ yarn at 55% and two 69d NOVAFIL® yarns at 11% into the airjet chamber. The denier of the 12 ply quoit yarn was measured to be 2667d.

This material was braided on a 13 carrier flat machine at a 12.3 pick. Its final denier was 18,467 of which 89.2% was quoit yarn and 19.1% was the nonabsorbable NOVAFIL® component.

The final non-sterile ligament had a breaking strength of 122 lbs (3.00 grams per denier) and an extension at break of 25.9%. Hydrolytic data indicates that this will make a viable product with a residual strength of 29.5 lbs.

Subsequent processing of the braid is as described above under the heading 'Description of the Preferred Embodiment'.

EXAMPLE 13

This implant design is identical to Example 11 except that in the initial 3 plying of the quoit yarns one end of a 226 denier MAXON ™/Heat Stretched Texturized DACRON® bicomponent yarn was substituted for one of the 219 denier MAXON ™ yarns. This MAXON ™ /Heat Stretched DACRON ® bicomponent was made by overfeeding a 66 denier MAXON ™ yarn at 55% and a 127 denier heat stretched DACRON ® yarn at 11% into the airjet chamber. The denier of the 12 ply quoit yarn measured 2613.

This material was braided on a 13 carrier flat machine at a 12.3 Pick. Its final non-sterile denier was 18,054, of which 89.0% was quoit yarn and 20.7% was the nonabsorbable heat stretched DACRON ® component.

The final non-sterile ligament had a breaking strength of 97 lbs (2.43 grams per denier) and an extension at break of 21.7%. Hydrolytic data indicated it would remain unchanged in strength for 14 days and would have a residual strength of 34.7 lbs.

Subsequent processing of the braid is as described above under the heading 'Description of the Preferred Embodiment'.

EXAMPLE 14

This construction consists of 100% MAXON ™ in a flat braid construction. It differs from previous constructions in that it is braided on a 21 carrier machine.

The sleeve yarn consists of 66 denier MAXON ™ yarn twisted to 1.4 TPI 'Z'. The 130 denier quoit yarns are first 2-plied at 2.8 TPI 'S'—then 5 yarns of this 2-ply construction ar TPI 'Z'. The final denier of the 10 ply quoit yarn is 1300.

The above yarns are then braided on a 21 carrier machine with 10 quoit yarns set at a 12 picks/inch. The final construction measures 16,986 denier, of which 91.8% is quoit yarn.

Samples are expected to have a non-sterile breaking strength of 124 lbs (equivalent to 3.31 grams per denier) with an extension at break of 35.2%.

EXAMPLE 15

This construction consists of 100% MAXON ™ in a flat braid construction. It differs from previous constructions in that it is braided on a 15 carrier machine.

The sleeve yarn consists of 98 denier MAXON ™ twisted to 1.4 TPI 'Z'. The 130 denier quoit yarns are 5-plied at the same level of twist to give a total denier of 650. All yarns are post treated after plying.

The above yarns are braided on a 45 carrier machine. Only 15 out of 45 available carriers are used for the sleeve yarns. All of the available 22 quoit positions are used. The braider is set for a 4.1 pick. The final construction measures 15,770 denier, of which 90.7% is parallel quoit yarn.

Straight pull tensile strength is expected to average approximately 168 lbs (4.83 grams/denier) with a 37.2% elongation at break.

EXAMPLE 16

This implant design is similar to Example 15 except that 1 yarn of heat stretched DACRON ® is substituted in ply twisting the quoit yarns. Also, all MAXON ™ yarns are post treated prior to twisting.

The final braid denier is 15,700, of which 90.7% is parallel quoit yarn. Approximately 18.1% of the total construction is the nonabsorbable DACRON ® component.

Straight pull tensile strength is expected to be approximately 127 lbs (3.67 grams/denier) with a breaking elongation of 29.3%. Hydrolytic data from similar constructions indicate that this design would make a viable product with a residual strength of 29 lbs due to the nonabsorbable component.

EXAMPLE 17

This design consists of 100% MAXON ™ in a flat braid construction. Although braided on a 45 carrier machine, it differs from Sample 15 in that it is 3.3 times heavier.

The sleeve yarns consist of 130 denier MAXON ™ twisted to 1.4 TPI 'Z'. The 130 denier quoit yarns were first 4-plied to 2.8 TPI 'Z', then four 4-ply yarns are reverse plied to 1.4 TPI 'S' to give a final quoit yarn denier of 2080. All yarns are post treated after twisting.

The above yarns are then braided on a 45 carrier machine using all available carriers for the sleeve and all of the available 22 quoit yarn positions. The braider is set for a 12.3 pick. The final construction measures 51,610 denier, of which 88.7% is parallel quoit yarn.

Straight pull tensile strength is expected to average 525 lbs (4.61 grams/denier) with a breaking elongation of 31.6%.

Although the following examples, and variations thereof, may be suitable for some soft tissue orthopedic (i.e. tendon) repair/reconstruction applications, they have been found to be inappropriate as ligament implants and therefore not part of this invention. They are disclosed for their comparative value to Examples 1-to-17, and as a contribution to the state of the art.

COMPARATIVE EXAMPLE A

This construction is a round bicomponent braid consisting of three braided elements.

a. A subcore which is a blend of 20/80 PGA/Heat Stretched DACRON ®. This subcore was made on an 8 carrier braider set at 5 picks/inch with each carrier containing a 1060 denier bicomponent yarn. The 1060 denier yarn was made by ply twisting 4 yarns of 210 denier heat stretched DACRON ® with 2 yarns of 110 denier DEXON ® (American Cyanamid Co., N.J. 07470, U.S.A.) at a low nominal level of twist. The preparation and polymeric composition of DEXON ® is disclosed in U.S. Pat. No. 3,297,033, which is incorporated herein by reference.

b. A core is also a blend of 20/80 PGA/Heat Stretched DACRON ®. This was made by braiding on a 12 carrier braider set at 5 picks/inch using the 8 carrier braid described above as a core. Each of the 12 carriers contained a 1270 denier bicomponent yarn which was made by ply twisting 5 yarns of 210 denier Heat Stretched DACRON ® with 2 yarns of 110 denier DEXON ® at a low level of twist.

c. The final sleeve was a blend of 60/40 PGA/Heat Stretched DACRON ®. This was made by braiding on a 16 carrier braider set at 15 picks per inch using the 12 carrier braid described above as a core. Each of the 16 carriers contained a 1510 denier bicomponent yarn which was made by ply twisting 3 yarns of 210 denier Heat Stretched DACRON ® with 8 yarns of 110 denier DEXON ® at a low level of twist.

All of the above yarns were post treated after ply twisting. This braid broke at 430 lbs straight pull (equivalent to 4.07 grams/denier) with an 18.8% extension at break. Braid denier was calculated to be 47,900.

Intramuscular and subcutaneous implants in canines exhibited little, if any, tissue ingrowth. Braids were encapsulated by unorganized collagen. This lack of vascularized cellular tissue and oriented collagen infiltration into the implant is considered undesirable for ligament repair or reconstruction. It is most probably a combined effect of: 1. the relatively short strength retention period of the PGA (i.e. 28 days); and 2. the tight round construction which minimizes implant-tissue interface area.

COMPARATIVE EXAMPLE B

This construction was basically the same as that in Comparative Example A except that the final sleeve was a 50/50 PGA/Heat Stretched DACRON® bicomponent yarn in a finer (more dispersed) blend. This was made on a 16 carrier braider set at 15 picks/inch using the 12 carrier braid described in Example A as a core. Each carrier contained a 1320 denier bicomponent yarn made by first ply twisting 1 yarn of 110 denier Heat Stretched DACRON® with 1 yarn of 110 denier DEXON®. Six of the 2-ply bicomponent yarns were then twisted to make the final 12-ply yarn. Twist levels were of a low order of magnitude.

The final braid denier was calculated to be 44.8K. The breaking strength measured 385 lbs (equivalent to 3.89 grams/denier) with a breaking elongation of 16.8%. Animal implant data were similar to Example A.

COMPARATIVE EXAMPLE C

This construction was, again, basically the same as in Comparative Example A except that the final sleeve had a coarser (less dispersed) configuration. It consisted of alternating a 1650 denier DACRON® (Heat Stretched) yarn with 1650 denier DEXON® yarn on each of the 16 carriers.

The final breaking strength was 429 lbs (equivalent to 3.88 grams/denier). The elongation at break was 17.8%. The final denier was calculated to be 50,100. Animal implant results were similar to Example A.

COMPARATIVE EXAMPLE D

This implant design was 100% DEXON® PGA in a round braid configuration and it consisted of three braided elements:

a. The subcore was made on an 8 carrier braider set at 5 picks/inch. Only 4 out of the eight sleeve carriers were used. The 440 denier yarn was made by plying four 110 denier yarns at a low number of twists per inch.

b. The core was made on an eight carrier machine also set at 5 picks/inch with all eight carriers containing a 550 denier yarn. The yarn was made by plying five 110 denier yarns at a low level of twist. The 4 carrier braid described above was used as a core.

c. The sleeve was made on a twelve carrier braider set at 15 picks/inch with all 12 carriers containing a 660 denier yarn. The yarn was made by plying six 110 denier yarns at a low level of twist. The eight carrier braid described above was used as a core.

The final denier was calculated to be 14,100. Tensile strength measured to be 134 lbs (equivalent to 4.32 grams/denier). The elongation at break was 33.4%.

Implant results

This material was implanted as a replacement for the resected patellar ligament of 10 month or older beagle dogs. At 1 and 2 months there was no histological evidence of tissue ingrowth. Braids were encapsulated by unorganized collagen and were structurally weak. This construction was abandoned since there was little hope for its use in ligament repair or replacement applications where ingrowth is desired.

COMPARATIVE EXAMPLE E

This implant design was 100% DEXON® (PGA) in a flat braid configuration and consisted of heavy denier quoit or warp yarns held together by light denier sleeve yarns:

a. Each quoit yarn contained 2214 denier DEXON® which was made by ply twisting three—123 denier yarns to give 369 denier yarn and then ply twisting six of these 369 denier yarns at 1.5 TPI 'S'.

b. The sleeve yarn contained 110 denier DEXON® yarns which were twisted to 10 TPI 'S'.

c. The braid was made on a thirteen carrier braider—each carrier containing 110 denier sleeve yarn which was braided about the 2214 denier warp yarns fed through all six available quoit positions. The total pick count was estimated at 10 per inch.

d. This construction was washed and post treated as a braid.

The total braid denier was approximately 15,100. Tensile strength measured 208 lbs. with a 22.3% elongation-to-break.

Devices of this design were implanted as replacements for the resected patellar ligament of 10 month or older beagle dogs in a comparative study with devices of Example 1. Histological evaluation at 1 and 2 months post-operatively revealed no significant tissue ingrowth or organization within the PGA implant. This lack of ligament repair was attributed to the relatively shorter in-vivo property retention period of the PGA material.

COMPARATIVE EXAMPLE F

This implant design was 100% DEXON® (PGA) in a flat braid configuration and again consisted of heavy denier quoit or warp yarns held together by light denier sleeve yarns. However, all the yarns were post treated; then air jet texturized prior to twisting and braiding.

a. The quoit (warp) yarn consisted of a 6 ply construction using 357 denier texturized DEXON® yarn to give a total 2142 denier yarn. This 357 denier yarn was made by entangling 3 ends of 110 denier DEXON® yarn—2 yarns with a 24% overfeed and one with a 6% overfeed.

b. The sleeve yarn was made similarly except it was a 152 denier, texturized DEXON® yarn. This was made by entangling 2 yarns of 62 denier DEXON®—one yarn with a 24% overfeed and the other with an 11% overfeed.

c. The braid was made on a thirteen carrier braider, each carrier containing the 152 denier yarn described in section b above. These sleeve yarns were braided about the 2142 denier warp yarns fed through all six available quoit positions. The total pick count was estimated at 12.3 per inch.

The total braid denier was 14,800. Tensile strength measured 152 lbs. with a 23.2% elongation-to-break.

Devices of this construction were evaluated in-vivo as described in the previous example. Upon sacrifice at 2 months, these implants were found to have better tissue ingrowth/organization than the non-texturized PGA devices of the previous example. However, the results achieved with implants made using the longer lasting GTMC yarns were consistently, significantly improved over those obtained with the devices of these comparative examples.

We claim:

1. A flat braided ligament or tendon implant device having a length to width ratio of greater than one, comprising a plurality of fibers, the majority of the fibers being in a direction essentially parallel to the implant length, the braid having about 5 to 25 carrier and up to about 10 warp yarns, wherein the yarns are texturized, and said implant having an absorbable component comprising from about 10 to 100 percent of a copolymer, the copolymer having glycolic acid ester and from about 20 to 40 percent by weight of trimethylene carbonate linkages, and the remainder of said implant, if any, having a nonabsorbable component.

* * * * *